United States Patent [19]

Brown et al.

[11] 4,156,726

[45] May 29, 1979

[54] 4-OXO-2-CARBOXYL QUINOLINE DERIVATIVES USED AS ANTIALLERGIC COMPOUNDS

[75] Inventors: Roger C. Brown; Hugh Cairns, both of Loughborough; Anthony R. Payne, Castle Donington, all of England

[73] Assignee: Fisons Limited, London, England

[21] Appl. No.: 635,615

[22] Filed: Nov. 26, 1975

[30] Foreign Application Priority Data

Dec. 7, 1974 [GB] United Kingdom ............... 53005/74
Dec. 7, 1974 [GB] United Kingdom ............... 53010/74
Dec. 7, 1974 [GB] United Kingdom ............... 53011/74

[51] Int. Cl.$^2$ ..................... A61K 31/47; C07D 215/48
[52] U.S. Cl. ..................... 424/258; 546/108; 546/110; 562/455; 562/433; 562/456; 562/457; 560/44
[58] Field of Search ....... 260/287 CF, 287 K, 283 BI, 260/283 SY; 424/258

[56] References Cited

U.S. PATENT DOCUMENTS

| | | | |
|---|---|---|---|
| 3,324,135 | 6/1967 | Lesher .................................. | 424/258 |
| 3,506,667 | 4/1970 | Kaminsky ..................... | 260/287 AN |
| 3,790,577 | 2/1974 | Waring ......................... | 260/287 CF |
| 3,901,895 | 8/1975 | Rhomberg et al. ........... | 260/287 CF |
| 3,932,416 | 1/1976 | Bays et al. ............................ | 424/258 |
| 3,966,743 | 6/1976 | Berger et al. ................. | 260/287 AN |
| 4,117,136 | 9/1978 | Hisada et al. .......................... | 424/258 |

FOREIGN PATENT DOCUMENTS

| | | | |
|---|---|---|---|
| 1912944 | 3/1969 | Fed. Rep. of Germany .... | 260/287 CF |
| 2145423 | 9/1970 | Fed. Rep. of Germany ..... | 260/283 BI |

OTHER PUBLICATIONS

Tokuyama et al., "JACS" 89, Feb. 1967, pp. 1017–1021.
Van. Loock et al., "J. of Org. Chem.", vol. 36, No. 17, 1971, pp. 2520–2524.
Morrison et al., Organic Chemistry, 1966, pp. 273, 278–280.

*Primary Examiner*—Donald G. Daus
*Assistant Examiner*—David E. Wheeler
*Attorney, Agent, or Firm*—Merriam, Marshall & Bicknell

[57] ABSTRACT

There are described compounds of formula I,

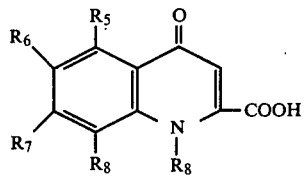

in which $R_5$ to $R_8$ may be a variety of substituents, or an adjacent pair of $R_5$, $R_6$, $R_7$ and $R_8$ form a chain —COCH=C(COOH)NRh—, or one of $R_5$, $R_6$, $R_7$ and $R_8$ form a group of formula II,

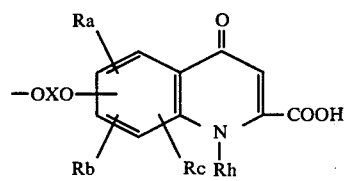

in which Ra, Rb and Rc have the same significances as $R_5$, $R_6$, $R_7$ and $R_8$, X is an optionally interrupted or substituted hydrocarbon chain, Rg and Rh, which may be the same or different are each alkyl, alkenyl, phenyl-alkyl, alkanoyl, benzoyl or phenylalkanoyl, or Rg and $R_8$ and/or Rh and Rc in formula II, together form a chain —(CH$_2$)$_n$—, and n is 2, 3 or 4.

There are also described processes for making the compounds and pharmaceutical, e.g. anti-allergic, compositions containing the compounds.

9 Claims, No Drawings

4-OXO-2-CARBOXYL QUINOLINE DERIVATIVES USED AS ANTIALLERGIC COMPOUNDS

This invention relates to new 4(1H)-quinoline derivatives, compositions containing them and methods for their preparation.

According to our invention we provide compounds of formula I,

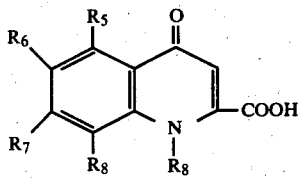

in which $R_5$, $R_6$, $R_7$ and $R_8$, which may be the same or different, each represent-hydrogen, alkyl, halogen, hydroxy, alkenyl, phenyl, alkoxy, alkenyloxy or phenylalkoxy; the alkyl, alkenyl, phenyl, alkoxy, alkenyloxy and phenylalkoxy groups optionally being substituted by a hydroxy, alkoxy, phenyl or halo group or by a 5 or 6 membered heterocyclic ring containing carbon and oxygen, or an adjacent pair of $R_5$, $R_6$, $R_7$ and $R_8$ form a chain —COCH=C(COOH)NRh—, or, together with the adjacent carbon atoms in the benzene ring, form a 5 or 6 membered carbocyclic ring, or one of $R_5$, $R_6$, $R_7$ and $R_8$ form a group of formula II,

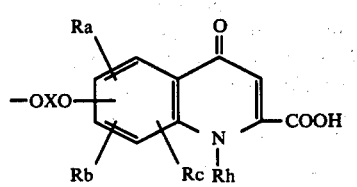

in which Ra, Rb and Rc have the same significances as $R_5$, $R_6$, $R_7$ and $R_8$, save that an adjacent-pair of Ra, Rb and Rc cannot form a chain —COCH=C-(COOH)NRh—, nor can an adjacent pair of Ra, Rb and Rc, together with the adjacent carbon atoms in the benzene ring, form a 5 or 6 membered carbocyclic ring, X is a hydrocarbon chain which may be interrupted by one or more oxygen atoms or carbonyl groups, or which may be substituted by a hydroxy or alkoxy group or by a halogen atom, Rg and Rh, which may be the same or different are each alkyl, alkenyl, phenyl-alkyl, alkanoyl, benzoyl or phenylalkanoyl, or Rg and $R_8$ and/or Rh and Rc is formula II, together form a chain —(CH$_2$)$_n$—, and n is 2, 3 or 4, provided that-when Rg is methyl or ethyl not all of $R_5$, $R_6$, $R_7$ and $R_8$ are hydrogen, and pharmaceutically acceptable derivatives thereof.

According to our invention we also provide a process for the production of a compound of formula I, or a pharmaceutically acceptable derivative thereof, which comprises (a) selectively hydrolysing or oxidising a compound of formula III,

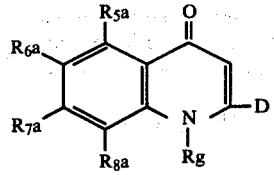

in which Rg and the proviso are as defined above, $R_{5a}$, $R_{6a}$, $R_{7a}$ and $R_{8a}$ have the same significances as $R_5$, $R_6$, $R_7$ and $R_8$ above, save than an adjacent pair of $R_{5a}$, $R_{6a}$, $R_{7a}$ and $R_{8a}$ may represent a chain of formula —COCH=C(D)NRh—, in which Rh is as defined above, or one of $R_{5a}$, $R_{6a}$, $R_{7a}$ and $R_{8a}$ may represent a group of formula IV,

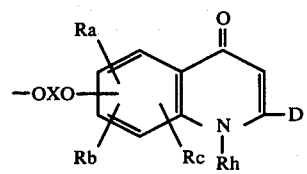

in which X, Ra, Rb, Rc and Rh are as defined above, and

D represents a group hydrolysable or oxidisable to a —COOH group, (b) producing a compound of formula I in which at least-one of Rg and Rh is an alkyl or a phenyl-alkyl group, by selective reduction of a corresponding compound of formula I, or an ester thereof, in which at least one of Rg and Rh is an alkenyl, alkanoyl or a phenylalkanoyl group.

(c) cyclising a compound of formula VIII or IX,

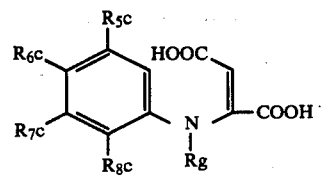

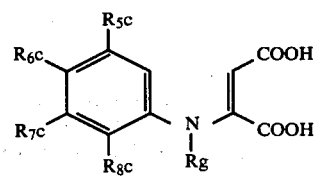

or an ester of either thereof, in which Rg and the proviso are as defined above, $R_{5c}$, $R_{6c}$, $R_{7c}$ and $R_{8c}$ have the same significances as $R_5$, $R_6$, $R_7$ and $R_8$ above, save that an adjacent pair of $R_{5c}$, $R_{6c}$, $R_{7c}$ and $R_{8c}$ may represent the pairs of groups —H and —NRhC(COOH)=CH—COOH, in which Rh is as defined above, or one of $R_{5c}$, $R_{6c}$, $R_{7c}$ and $R_{8c}$ may represent a group of formula X,

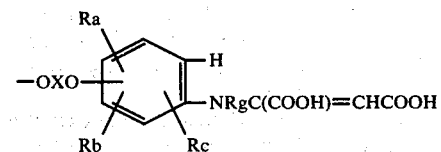

or an ester thereof,
in which X, Ra, Rb, Rc and Rg are as defined above,
(d) producing a compound of formula I in which X is a hydrocarbon chain optionally substituted by an —OH group,
by reacting a compound of formula XI,

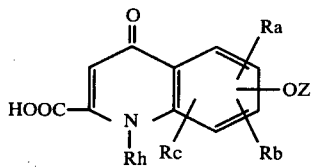

or an ester thereof,
in which Ra, Rb, Rc and Rh are as defined above, and Z is hydrogen or a metallic cation, or is a hydrocarbon chain carrying an anion forming group or an epoxide group,
with a compound of formula XII,

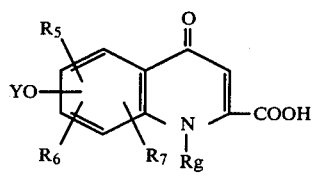

or an ester thereof,
in which $R_5$, $R_6$, $R_7$ and $R_g$ are as defined above, and Y represents hydrogen or a metallic cation when Z represents a hydrocarbon chain carrying an anion forming group or an epoxide group, and, when Z represents hydrogen or a metallic cation, Y represents a hydrocarbon chain carrying an anion forming group or an epoxide group,
or (e) cyclising a compound of formula XV,

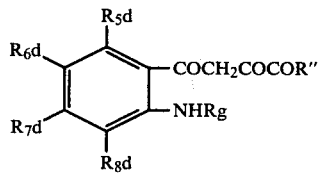

in which Rg is as defined above, R" is an —OH group or a group hydrolysable thereto,
$R_{5d}$, $R_{6d}$, $R_{7d}$ and $R_{8d}$ have the same significances as $R_5$, $R_6$, $R_7$ and $R_8$ above, save that an adjacent pair of $R_{5d}$, $R_{6d}$, $R_{7d}$ and $R_{8d}$ may represent the pair of groups —NHRh and —COCH$_2$COCR", in which Rh and R" are as defined above, or one of $R_{5d}$, $R_{6d}$, $R_{7d}$ and $R_{8d}$ may represent a group of formula XVI,

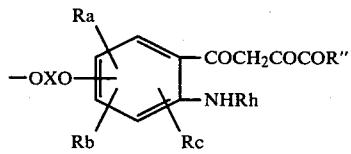

in which Ra, Rb, Rc, Rh and R" are as defined above,
and where desired or necessary converting the compound of formula I to a pharmaceutically acceptable derivative thereof, or vice versa.

In process (a) the group D may be, for example, an ester, acid halide, amide or nitrile group, which may be hydrolysed to a —COOH group. The hydrolysis may be carried out using conventional techniques, for example under basic conditions, e.g. using sodium carbonate, sodium hydroxide, or sodium bicarbonate, or under acidic conditions, e.g. using a mixture of aqueous dioxan and hydrochloric acid, or hydrogen bromide in acetic acid. The hydrolysis may be carried out at a temperature of from about 25° to 120° depending on the compounds used. Alternatively the group D may be an alkyl, e.g. a lower alkyl such as methyl, a hydroxymethyl, an aralkenyl, e.g. styryl, an acyl, e.g. a lower alkanoyl such as acetyl, or a formyl group. The oxidation may be carried out using conventional techniques which do not otherwise modify the molecule to such an extent that the yield of the desired product is uneconomical, for example an alkyl or a hydroxymethyl group may be oxidised using selenium dioxide, e.g. under reflux in aqueous dioxan; or chromic acid, e.g. under reflux in aqueous acetic acid. Aralkenyl groups may be oxidised using, for example neutral or alkaline potassium permanganate in aqueous ethanol, and acyl groups may be oxidised using, for example chromic acid or an aqueous hypochlorite, e.g. sodium hypochlorite. The formyl group may be oxidised using, for example chromic acid or silver oxide.

In process (b) the selective reduction may be carried out chemically using, for example, lithium aluminum hydride in a solvent which is inert under the reaction conditions, e.g. diethyl ether or tetrahydrofuran. The reaction using lithium aluminium hydride is of course carried out under anhydrous conditions and is preferably carried out at a temperature of from about −10° to 50° C. Alternatively the reduction may be carried out catalytically, e.g. using a palladium on charcoal catalyst. When one or both Rg and Rh are methyl the corresponding compound in which one or both of Rg and Rh are formyl may be reduced by known methods for the reduction of a formyl group to a methyl group, e.g. treatment with formic acid at an elevated temperature of, for example, about 80° to 120° C.

In process (c) the cyclisation may be carried out by treating the compound of formula VIII or IX, or a corresponding compound containing one fumaric acid moiety and one maleic acid moiety, or a mixture thereof, with a cyclising agent, for example a dehydrating agent such as chlorosulphonic, sulphuric, or preferably polyphosphoric acid. The reaction is preferably carried out under anhydrous conditions and may be carried out at a temperature of from about 25° to 150°, and preferably from 75° to 150° C. We have found that isomerisation of the maleic acid derivative of formula IX to the corresponding fumaric acid derivative of formula VIII takes place when polyphosphoric acid is used to cyclise these compounds to a compound of formula I, thus enabling a satisfactory yield of the compound of formula I to be obtained from a prima facie unsatisfactory mixture of compounds of formula VIII, IX and their unsymmetrical isomers.

In process (d) when Y or Z is a metallic cation the cation may be that of, for example, an alkali metal, e.g. sodium or another reactive metal, e.g. thallium. When Y or Z represent a hydrocarbon chain carrying an anion forming group the anion forming group may be, for example, a halogen atom, e.g. bromine, or a sulphonate group, e.g. a methyl sulphonate or a p-toluenesulphonate group. When Y or Z represents a hydrocarbon chain carrying a halogen atom the reaction may be carried out in the presence of a solvent which is inert under the reaction conditions, e.g. acetone and in the presence of an acid acceptor, e.g. potassium carbonate. The reaction is also preferably carried out under anhydrous conditions and in the presence of a suitable catalyst, e.g. KI. When Y or Z represent a hydrocarbon group carrying an epoxide the reaction may be carried out at an elevated temperature in a solvent which is inert under the reaction conditions, e.g. dioxan or dimethylformamide, and in the presence of a suitable catalyst, e.g. trimethylbenzylammonium hydroxide.

In process (e) the cyclisation may be carried out under acidic or neutral conditions. It is however preferred to carry out the cyclisation in the presence of a base, e.g. sodium hydroxide, in a suitable solvent, e.g. water. The reaction may be carried out at from about 20° to 150° C. The group —COR" is preferably an ester group, e.g. R" may be a lower alkoxy group. We prefer to carry out process (e) by ring opening a starting material of formula XVII,

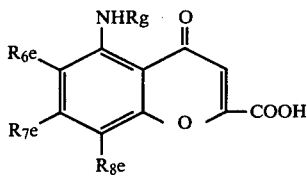

XVII or an ester thereof, in which $R_{5e}$, $R_{6e}$, $R_{7e}$ and $R_{8e}$ have the same significances as $R_6$, $R_7$ and $R_8$ above, save that one of $R_{6e}$, $R_{7e}$ and $R_{8e}$ may be a group of formula XVIII,

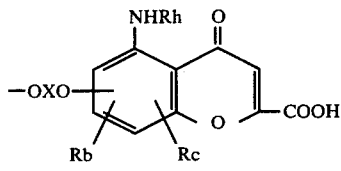

XVIII or an ester thereof,
in which Rb, Rc, Rh and X are as defined above,
to produce the compound of formula XV. The ring opening may be carried out using a strong base, e.g. sodium hydroxide. The compound of formula XV may be isolated, but is preferably cyclised to a compound of formula I without isolation.

In process (b), (c) and (d) when an ester starting material is used the ester may be, for example, a C 1 to 10 alkyl ester.

The starting materials for processes (a) and (c) may be made by reacting a compound of formula IV,

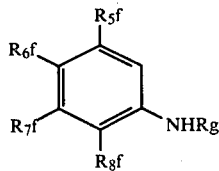

IV in which Rg and the proviso are as defined above, and
$R_5f$, $R_6f$, $R_7f$ and $R_8f$ have the same significances as $R_5$, $R_6$, $R_7$ and $R_8$ above, save that an adjacent pair of $R_5f$, $R_6f$, $R_7f$ and $R_8f$ may represent the pair of groups —H and —NHRh, in which Rh is as defined above, or one of $R_5f$, $R_6f$, $R_7f$ and $R_8f$ may represent a group of formula XIII,

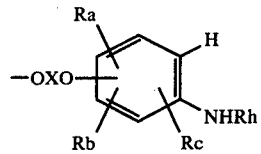

XIII in which X, Ra, Rb, Rc and Rh are as defined above, with a compound of formula VII, Da—C—C—Da           VII in which Da is an ester group,
to produce a mixture of compounds of formulae V and VI,

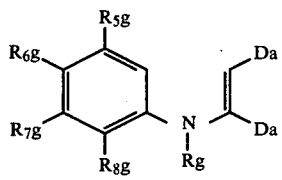

V

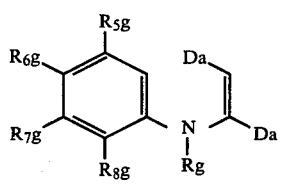

VI in which Rg, Da and the proviso are as defined above, and
$R_5g$, $R_6g$, $R_7g$ and $R_8g$ have the same significances as $R_5$, $R_6$, $R_7$ and $R_8$, save that an adjacent pair of $R_5g$, $R_6g$, $R_7g$ and $R_8g$ may represent the pair of groups —H and —NRhCDa=CHDa, in which Rh is as defined above, or one of $R_5g$, $R_6g$, $R_7g$ and $R_8g$ may represent a group of formula XIV,

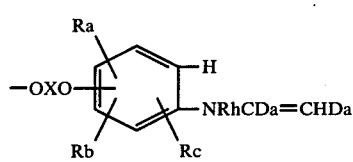

XIV in which X, Ra, Rb, Rc, Rh and Da are as defined above, and the corresponding unsymmetrical compounds containing one fumarate ester and one maleate ester moiety respectively.

The compounds of formula V and VI and the corresponding unsymmetrical compounds may be hydrolysed to give compounds of formulae IX and VIII and the corresponding unsymmetrical compounds containing one fumaric acid and one maleic acid moiety respectively. Alternatively the groups Da in the compounds of formulae V and VI etc may be converted using conventional techniques known per se, to other groups D and the resulting compounds cyclised, using the same conditions as for process (c) above, to yield the desired compound of formula II. As a further and preferred alternative the compounds of formula V and VI or the corresponding unsymmetrical compounds may be cyclised, using the same conditions as for process (c) above, to give a compound of formula II in which D is an ester group, and the resulting compound of formula II used itself in process (a), or the D group converted to another group D, e.g. an acid halide, amide or nitrile group, using techniques known per se.

The fumarate isomer of formula VI (or the corresponding compound in which Da has been converted to D) is the only isomer which can cyclise to give the required compounds of formula II. The proportion of the two isomers may be readily determined by nuclear magnetic resonnance spectroscopy and we have found that, in general, the desired fumaric acid derivative is only a minor proportion of the mixture of isomers obtained from the reaction.

Compounds of formula IV may be made from known compounds using conventional techniques known per se. Compounds of formulae XI and XII may be made from known compounds by a series of steps ending in processes analogous to processes (a), (b) or (c) above.

Compounds of formula XV may, in addition to the process set out above, be made by conventional techniques known per se, e.g. by reaction of an appropriate o-amino-acetophenone with, for example, a dialkyloxalate such as diethyl oxalate.

Some of the groups $R_5$, $R_6$, $R_7$, $R_8$, Ra, Rb, Rc, Rg, Rh and X may be affected by the reaction conditions described above. Where necessary or desired therefore the reaction may be carried out using protected derivatives of the reagents, e.g. the formyl derivative of an —OH group.

The processes as described above may produce the compound of formula I or a derivative thereof. It is also within the scope of this invention to treat any derivative so produced to liberate the free compound of formula I, or to convert one derivative into another.

Pharmaceutically acceptable derivatives of the compounds of formula I include pharmaceutically acceptable salts. Suitable salts include water soluble salts, for example salts with suitable organic bases, e.g. salts with lower (C 1 to 6)alkyl amines, e.g. methylamine or ethylamine, with hydroxy substituted C 1 to 6 alkylamines, or with simple monocyclic nitrogen heterocyclic compounds, e.g. piperidine or morpholine, and preferably with inorganic cations, e.g. ammonium, alkali metal (e.g. sodium and potassium) and alkaline earth metal (e.g. calcium and magnesium) salts. Other pharmaceutically acceptable derivatives which may be mentioned include esters, e.g. C 1 to 10 alkyl and C 1 to 10 phenylalkyl esters; and amides, e.g. derived from mono- or dilower alkyl amines or ammonia.

The compounds of formula I, and pharmaceutically acceptable derivatives thereof, are useful because they possess pharmacological activity in animals; in particular they are useful because they inhibit the release and/or action of pharmacological mediators which result from the in vivo combination of certain types of antibody and specific antigen, e.g. the combination of reaginic antibody with specific antigen. (See Example 27 of British Patent Specification No. 1,292,601).

In man, both subjective and objective changes which result from inhalation of specific antigen by sensitised subjects are inhibited by prior administration of the new compounds. Thus the new compounds are useful in the treatment of asthma, e.g. allergic asthma. The new compounds are also of use in the treatment of so-called 'intrinsic' asthma (in which no sensitivity to extrinsic antigen can be demonstrated). The new compounds are also of value in the treatment of other conditions in which antigen-antibody reactions are responsible for disease, for example hay fever; certain eye conditions, e.g. trachoma; alimentary allergy, e.g. urticaria and atopic eczema; and gastrointestinal allergy, especially in children, e.g. milk allergy.

For the above mentioned uses the dosage administered will, of course, vary with the compound employed, the mode of administration and the treatment desired, However, in general, satisfactory results are obtained when the compounds are administered at a dosage of from 0.1 to 50 mg per kg of animal body weight in the test set out in Example 27 of British Patent Specification No. 1,292,601. For man the total daily dosage is in the range of from about 1 mg to 3,500 mg which may be administered in divided doses from 1 to 6 times a day or in sustained release form. Thus unit dosage forms suitable for administration (by inhalation or oesophageally) comprise from about 0.17 mg to 600 mg of the compound admixed with a solid or liquid pharmaceutically acceptable diluent or carrier.

According to our invention we also provide a pharmaceutical composition comprising (preferably a minor proportion of) a compound of formula I, or a pharmaceutically acceptable derivative thereof, in combination with a pharmaceutically acceptable adjuvant, diluent or carrier. Examples of suitable adjuvants, diluents or carriers are:- for tablets and dragées; lactose, starch, talc or stearic acid; for capsules, tartaric acid or lactose; for suppositories, natural or hardened oils or waxes; for inhalation coarse lactose; and for topical application, wool fat, soft paraffin or a cream BP. For use in such compositions, the compound of formula I, or the pharmaceutically acceptable derivative thereof, preferably has a mass medium diameter of from 0.01 to 10 microns. The compositions may also contain suitable preserving, stabilising and wetting agents, solubilizers, sweetening and colouring agents and flavourings. The compositions may, if desired, be formulated in sustained release form.

According to the invention there is also provided a process for the preparation of a pharmaceutically acceptable salt of a compound of formula I, which comprises treating a compound of formula I, or another salt thereof, with a compound containing an available pharmaceutically acceptable cation, e.g. a base or an ion exchange resin, containing a sodium potassium, calcium, ammonium or an appropriate nitrogen containing organic cation. In general we prefer to form the pharmaceutically acceptable salt by treating the free acid of formula I with an appropriate base, e.g. with an alkaline-earth or alkali metal hydroxide, carbonate or bicarbonate in aqueous solution, or by treating another salt of a compound of formula I with an appropriate salt by a metathetical process. When a strongly basic compound is used care should be taken, e.g. by keeping the temperature sufficiently low, to ensure that the compound of formula I is not hydrolysed or otherwise degraded. The pharmaceutically acceptable salt may be recovered from the reaction mixture by, for example, solvent precipitation and/or removal of the solvent by evaporation, e.g. by freeze drying.

In compounds of formula I it is preferred that $R_5$, $R_6$, $R_7$ and $R_8$ should, when they contain carbon, each contain up to 8 and more preferably up to 4 carbon atoms or that an adjacent pair of $R_5$, $R_6$, $R_7$ and $R_8$, preferably $R_7$ and $R_8$ form a —$CH_2CH_2CH_2CH_2$— chain.

It is also preferred that Rg and Rh should each contain up to 10 carbon atoms. Particular values of Rg and Rh which may be mentioned are methyl, ethyl, acetyl, propionyl and benzoyl.

The term alkanoyl as used with respect to Rg and Rh is used to include the formyl group.

In compounds of formula I in which one of $R_5$, $R_6$, $R_7$ and $R_8$ form a group of formula II, it is preferred that not more than one of Ra, Rb and Rc, and not more than one of the remainder of $R_5$, $R_6$, $R_7$ and $R_8$ is other than hydrogen.

It is preferred that Ra, Rb Rc and the remainder of $R_5$, $R_6$, $R_7$ and $R_8$ are selected from hydrogen, halogen, alkyl, hydroxy, alkenyl, alkenyloxy, phenyl, alkoxy, hydroxy-alkoxy, alkoxy-alkoxy halo-alkyl or tetrahydrofurfuryloxy. It is also preferred that Ra to Rc should, when they contain carbon, each contain up to 8 carbon atoms.

Particularly preferred compounds containing a group of formula II are those in which all of Ra, Rb, Rc, and the remainder of $R_5$, $R_6$, $R_7$ and $R_8$ are hydrogen.

The group X may be a straight or branched, saturated or ethylenically unsaturated hydrocarbon chain. Further, X may be such a chain interrupted by one or more oxygen atoms or carbonyl groups and may be substituted by one or more halogen atoms (e.g. chlorine or bromine atoms), or hydroxy, or alkoxy C 1 to 6 groups. The group X preferably contains from 2 to 10, and more preferably 3 to 7, carbon atoms. Thus X is desirably an alkylene chain containing from 3 to 7 carbon atoms, which chain is optionally substituted by an —OH group. Specific examples of —X— groups are:

—(CH$_2$)$_3$—

—(CH$_2$)$_5$—

—CH$_2$CHOHCH$_2$—

—CH$_2$CH$_2$CHOHCH$_2$CH$_2$—

The chain —O—X—O— may link different or corresponding positions on the quinolone nuclei, but preferably links the 5,5'-positions.

In compounds of formula I in which an adjacent pair of $R_5$, $R_6$, $R_7$ and $R_8$ form a —COCH=C(COOH)—NRh— chain, we prefer one of the remainder of $R_5$, $R_6$, $R_7$ and $R_8$ to be alkoxy or alkyl. Specific examples of $R_5$, $R_6$, $R_7$ and $R_8$ are hydrogen, methoxy, hydroxy, ethyl, butyl, bromine, chlorine and allyloxy. We prefer those compounds in which $R_6$ and $R_7$ and more preferably $R_7$ and $R_8$, form a chain —COCH=C(COOH)—NRh—. We also prefer those compounds in which the —NRh— of the chain formed by an adjacent pair of $R_6$, $R_7$ and $R_8$ is attached to the $R_7$ position.

The invention is illustrated, but in no way limited by the following Examples in which the temperatures are in degrees centigrade.

EXAMPLE 1

1-Ethyl-7,8,9,10-tetrahydro-5-hydroxy-6-propyl-4(1H)-benzo[h] quinolinone-2-carboxylic Ethyl 5-aminoethyl-6,7,8,9-tetrahydro-4-oxo-10-propyl-naphtho [2,3-b]pyran-2-carboxylate (6.0g; 16.6 mmole) was heated on a steam bath with 2M sodium hydroxide solution (65 ml) for 1 hour. The solution was acidified with concentrated hydrochloric acid and the orange solid was filtered off, dried and recrystallised from toluene to yield an analytically pure sample of the title compound (3.7g; 68%) mp 209°–10°, mass spectrum m+ 329; p+ 300; 285; 272; 256; 226.

Sodium 1-ethyl-7,8,9,10-tetrahydro-5-hydroxy-6-propyl-4(1H)-benzo [h]quinolinone-2-carboxylate The quinolinone acid product of step (a) (2.5g; 7.35 mmole) was dissolved in a solution of sodium bicarbonate (617 mg; 7.35 mmole) in water (25 ml). The resulting solution was freeze-dried to yield a pure sample of the title sodium salt hydrated with .7.7% (w/w) of water.

EXAMPLE 2

1-Ethyl-5-hydroxy-6-propyl-7,8,9,10-tetrahydro-4(1H)-benzo[h] quinolinone-2-carboxylic acid Benzyltrimethylammonium hydroxide (40% aqueous solution) (3 drops) was added to a stirred solution of 1-ethylamino-3-hydroxy-4-propyl-5,6,7,8-tetrahydronaphthalene (2.33g) and dimethyl acetylene dicarboxylate (1.42g) in methanol (10 ml). The mixture was heated at reflux for 8 hours, cooled, filtered and the methanol removed in vacuo. The resulting oil, a mixture of the cis and trans tetrahydronaphthylamino acrylic acid esters, was heated on a steam bath with polyphosphoric acid (10g) for 2 hours. The mixture was cooled, poured into water and the solution adjusted to pH7 with sodium bicarbonate. The resulting mixture was extracted with ethyl acetate. The extracts were dried (magnesium sulphate) and evaporated in vacuo giving crude tetrahydrobenzo quinolinone-2-carboxylic acid methyl ester as a sticky solid.

To this crude ester was added sodium bicarbonate (1g), water (100 ml) and ethanol (15 ml) and the resulting mixture heated at reflux for 4 hours. After cooling the mixture was filtered and the ethanol removed from the filtrate in vacuo. Acidification of the resulting aqueous solution with dilute hydrochloric acid gave a precipitate which on crystallisation from toluene gave the title compound as a yellow solid, mp 209–210.

The following compounds may also be made by the process of the invention:

6,8-Diethyl-5-hydroxy-1-methyl-4(1H)-quinolinone-2-carboxylic acid.

1-Ethyl-6,7,8,9-tetrahydro-5-hydroxy-10-propyl-benzo[g] quinolinone-2-carboxylic acid.

1,3-Bis(2-carboxy-1-methyl-4(1H)-quinolinone-5-yloxy)propan-2-ol.

1,4,7,10-Tetrahydro-5-methoxy-1,7-dimethyl-4,10-dioxophenanthroline-2,8-dicarboxylic acid.

1,4,7,10-Tetrahydro-6-butyl-1,7-dimethyl-4,10-dioxo-phenanthroline-2,8-dicarboxylic acid.

We claim:

1. A compound having the formula

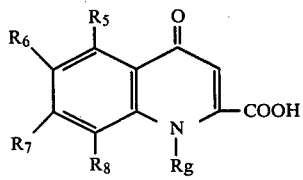

in which $R_5$, $R_6$, $R_7$ and $R_8$, which may be the same or different, each represent hydrogen, sterically compatible $C_1$-$C_8$ alkyl, halogen, or hydroxy, provided that an adjacent pair or $R_5$, $R_6$, $R_7$ and $R_8$ together with the adjacent carbon atoms in the benzene ring, form a saturated 5 or 6 membered carbocyclic ring, Rg is alkyl having up to 10 carbon atoms, and pharmaceutically acceptable salts, pharmaceutically acceptable $C_1$-$C_{10}$ alkyl esters, and pharmaceutically acceptable amides derived from ammonia or lower alkyl amines, of said compound.

2. A compound according to claim 1, wherein $R_5$, $R_6$, $R_7$ and $R_8$, when they contain carbon, each have up to 4 carbon atoms.

3. A compound according to claim 1, wherein an adjacent pair of $R_5$, $R_6$, $R_7$ and $R_8$ forms a —$CH_2CH_2CH_2CH_2$— chain.

4. A compound according to claim 3, wherein $R_7$ and $R_8$ together form a —$CH_2CH_2CH_2CH_2$— chain.

5. A compound according to claim 1, wherein $R_g$ is selected from methyl, or ethyl.

6. A compound according to claim 1 which is 1-ethyl-7,8,9,10-tetrahydro-5-hydroxy-6-propyl-4(1H)-benzo[h-]quinolinone-2-carboxylic acid.

7. A compound according to claim 1 which is 1-ethyl-6,7,8,9-tetrahydro-5-hydroxy-10-propyl-benzo[g-]quinolinone-2-carboxylic acid.

8. A pharmaceutical composition comprising an effective anti antibody-antigen reaction amount of a compound according to claim 1 in admixture with a pharmaceutically acceptable adjuvant, diluent or carrier.

9. A method of treatment of a condition in which an antibody-antigen reaction is responsible for disease, which comprises treatment of a subject suffering, or liable to suffer, from such a condition by administering topically or per os an effective anti antibody-antigen reaction amount of a compound according to claim 1.

* * * * *

UNITED STATES PATENT AND TRADEMARK OFFICE
CERTIFICATE OF CORRECTION

PATENT NO. : 4,156,726
DATED : May 29, 1979
INVENTOR(S) : ROGER C. BROWN ET AL.

It is certified that error appears in the above-identified patent and that said Letters Patent are hereby corrected as shown below:

In the Abstract, Formula I, "$\underset{\underset{R_8}{|}}{N}$"

should be $--\underset{\underset{R_9}{|}}{N}--$.

Col. 1, Formula I, "$\underset{\underset{R_8}{|}}{N}$" should be $--\underset{\underset{R_9}{|}}{N}--$.

Col. 11, line 6 (Claim 2) "contain" should be --have--.

Col. 11, line 6, (Claim 2), "have" should be --has--.

Signed and Sealed this

Ninth Day of October 1979

[SEAL]

Attest:

RUTH C. MASON
Attesting Officer

LUTRELLE F. PARKER
Acting Commissioner of Patents and Trademarks